United States Patent
Schuster et al.

(10) Patent No.: US 11,529,616 B2
(45) Date of Patent: Dec. 20, 2022

(54) CATALYST SYSTEM AND PROCESS FOR PREPARING DIMETHYL ETHER

(71) Applicant: BASF SE, Ludwigshafen am Rhein (DE)

(72) Inventors: Sabine Schuster, Ludwigshafen am Rhein (DE); Ekkehard Schwab, Ludwigshafen am Rhein (DE); Stefan Altwasser, Ludwigshafen am Rhein (DE); Harry Kaiser, Heidelberg (DE); Stephan A. Schunk, Heidelberg (DE); Manuela Gaab, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 141 days.

(21) Appl. No.: 16/956,668

(22) PCT Filed: Dec. 20, 2018

(86) PCT No.: PCT/EP2018/086095
§ 371 (c)(1),
(2) Date: Jun. 22, 2020

(87) PCT Pub. No.: WO2019/122078
PCT Pub. Date: Jun. 27, 2019

(65) Prior Publication Data
US 2020/0316570 A1 Oct. 8, 2020

(30) Foreign Application Priority Data
Dec. 20, 2017 (EP) .................................. 17208927

(51) Int. Cl.
| | | |
|---|---|---|
| *B01J 29/06* | (2006.01) | |
| *B01J 29/46* | (2006.01) | |
| *B01J 8/06* | (2006.01) | |
| *C07C 41/01* | (2006.01) | |
| *C07C 43/04* | (2006.01) | |
| *B01J 37/00* | (2006.01) | |
| *B01J 35/02* | (2006.01) | |
| *B01J 35/00* | (2006.01) | |
| *C07C 41/09* | (2006.01) | |

(52) U.S. Cl.
CPC ................ *B01J 29/46* (2013.01); *B01J 8/06* (2013.01); *B01J 35/0006* (2013.01); *B01J 35/023* (2013.01); *B01J 37/0009* (2013.01); *B01J 37/0063* (2013.01); *C07C 41/01* (2013.01); *C07C 41/09* (2013.01); *C07C 43/043* (2013.01); *C07C 2529/76* (2013.01)

(58) Field of Classification Search
CPC .......... B01J 8/06; B01J 29/46; B01J 35/0006; B01J 35/002; B01J 35/023; B01J 37/0063; B01J 37/0244; B01J 37/0246; B01J 37/0009; C07C 41/01; C07C 41/09; C07C 43/043; C07C 2529/76
USPC ............... 502/60, 63, 64, 66, 69, 71, 74, 77; 518/700, 702; 568/698; 585/324; 422/149, 187, 600, 630, 631, 632, 634, 422/635, 638, 639, 641, 644, 650, 651, 422/652, 653
See application file for complete search history.

(56) References Cited

U.S. PATENT DOCUMENTS

| | | | |
|---|---|---|---|
| 6,147,125 A | 11/2000 | Shikada et al. | |
| 6,638,892 B1 | 10/2003 | Wu et al. | |
| 2013/0210612 A1 | 8/2013 | Schäfer et al. | |
| 2013/0211147 A1* | 8/2013 | Cheiky | B01J 21/16 502/68 |
| 2014/0171691 A1* | 6/2014 | Kortan | C10G 3/49 585/324 |
| 2016/0318006 A1* | 11/2016 | Malyala | B01J 23/80 |

FOREIGN PATENT DOCUMENTS

| | | |
|---|---|---|
| CN | 1883804 A | 12/2006 |
| EP | 0483609 A1 | 5/1992 |
| EP | 1238701 A1 | 9/2002 |
| RU | 2528409 C1 | 9/2014 |
| RU | 2624015 C2 | 6/2017 |
| WO | 03/89392 A1 | 10/2003 |
| WO | 2013/120938 A1 | 8/2013 |
| WO | 2013/120945 A1 | 8/2013 |
| WO | 2013/160133 A1 | 10/2013 |
| WO | 2014/174107 | * 10/2014 |

OTHER PUBLICATIONS

Abu-Dahrieh et al., "Activity and deactivation studies for direct dimethyl ether synthesis using CuO—ZnO—Al2O3 with NH(4)ZSM-5, HZSM-5 or gamma-Al2O3", Chem. Eng. J., vol. 203, No. 1, 2012, pp. 201-211.

Loosdrecht et al., "Synthesis gas to hydrogen, methanol, and synthetic fuels", In X Robert Schlogl (Ed.), Chemical energy storage, 2013, pp. 443-458.

Ohno et al., "Slurry phase DME direct synthesis technology—100 tons/day demonstration plant operation and scale up study-" Natural Gas Conversion VIII, 2007, pp. 403-408.

Peng et al., "A novel mechanism of catalyst deactivation in liquid phase synthesis Gas-to-DME reactions", Studies Surf. Sci. Cat., vol. 111, 1997, pp. 175-182.

\* cited by examiner

*Primary Examiner* — Elizabeth D Wood
(74) *Attorney, Agent, or Firm* — Faegre Drinker Biddle & Reath LLP

(57) ABSTRACT

The invention relates to a catalyst system and process for preparing dimethyl ether from synthesis gas as well as the use of the catalyst system in this process.

14 Claims, No Drawings

CATALYST SYSTEM AND PROCESS FOR PREPARING DIMETHYL ETHER

CROSS-REFERENCE TO RELATED APPLICATIONS

This application is a national stage application (under 35 U.S.C. § 371) of PCT/EP2018/086095, filed Dec. 20, 2018, which claims benefit of European Application No. 17208927.8, filed Dec. 20, 2017, both of which are incorporated herein by reference in their entirety.

The invention relates to a catalyst system and process for preparing dimethyl ether from synthesis gas as well as the use of the catalyst system in this process.

Hydrocarbons are essential in modern life and used as fuel and raw materials, including the chemical, petrochemical, plastics and rubber industry. Fossil fuels such as oil and natural gas are composed of hydrocarbons with a specific ratio of carbon to hydrogen. Despite their wide application and high demand, fossil fuels also have limitations and disadvantages in view of being a finite resource and their contribution to global warming if they are burned.

Research on alternative fuels was mainly started due to ecological and economical considerations. Among the alternative fuels, dimethyl ether (DME), which was recently discovered as a clean fuel, can be synthesized from synthetic gas which was generated from different primary sources. These primary sources can be natural gas, coal, heavy oil, and also biomass. Up to now, only two DME synthesis procedures from synthesis gas have been claimed, one of these being the traditional methanol synthesis, followed by a dehydration step, and the other being a direct conversion of synthesis gas to DME in one single step.

Recently attention has been directed towards the direct synthesis of dimethyl ether from synthesis gas, using a catalytic system that combines a methanol synthesis catalyst and a catalyst for dehydration of said alcohol. It was confirmed on the basis of experimental studies that both the stage of methanol synthesis and the stage of methanol dehydration could be conducted simultaneously on one appropriate catalytic system. Depending upon the applied synthesis gas, the catalyst might additionally show water gas shift activity.

Most known methods of producing methanol involve synthesis gas. Synthesis gas is a mixture of mainly hydrogen, carbon monoxide and carbon dioxide, from which methanol is produced over a catalyst.

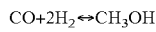
CO+2H$_2$↔CH$_3$OH

In a following step methanol can be converted into DME by dehydration over an acidic catalyst.

2CH$_3$OH↔CH$_3$OCH$_3$+H$_2$O

In the direct DME production there are mainly two overall reactions that occur from synthesis gas. These reactions, reaction (1) and reaction (2), are listed below.

3CO+3H$_2$↔CH$_3$OCH$_3$+CO$_2$ (1)

2CO+4H$_2$↔CH$_3$OCH$_3$+H$_2$O (2)

Reaction (1) occurs with the combination of three reactions, which are methanol synthesis reaction, methanol dehydration reaction, and water gas shift reaction:

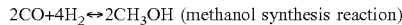
2CO+4H$_2$↔2CH$_3$OH (methanol synthesis reaction)

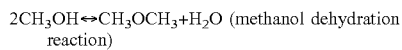
2CH$_3$OH↔CH$_3$OCH$_3$+H$_2$O (methanol dehydration reaction)

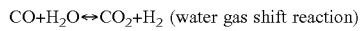
CO+H$_2$O↔CO$_2$+H$_2$ (water gas shift reaction)

Reaction (1) has a stoichiometric ratio H$_2$/CO of 1:1 and has some advantages over reaction (2). For example, reaction (1) generally allows higher single pass conversions and less energy-consuming in comparison to the removal of water from the system in reaction (2).

Methods for the preparation of dimethyl ether are well-known from prior art. Several methods are described in the literature where DME is produced directly in combination with methanol by the use of a catalyst active body in both the synthesis of methanol from synthesis gas and methanol dehydration. Suitable catalysts for the use in the synthesis gas conversion stage include conventionally employed methanol catalyst such as copper and/or zinc and/or chromium-based catalyst and methanol dehydration catalyst.

WO 2013/120938 relates to a catalytically active body for the synthesis for dimethyl ether from synthesis gas. In the introductory part of this document, several prior art references are discussed which disclose different catalysts and process options for this process.

Chemical Engineering Journal 203 (2012), pages 201 to 211, discloses activity and deactivation studies for direct dimethyl ether synthesis using Cu—ZnO—Al$_2$O$_3$ with NH$_4$ZSM-5, HZSM-5 or γ-Al$_2$O$_3$. The catalyst system is employed for the production of dimethyl ether from syngas. It was found that of the solid acids which are necessary for the dehydration function of the admixed system, the CuO—ZnO—Al$_2$O$_3$/HZSM-5 bifunctional catalyst showed highest stability over a continuous period of 212 h. This particular system was observed to lose around 16.2% of its initial activity over this operating period.

Studies Surf. Sci. Cat. 111 (1997), pages 175 to 182, discloses a slurry-phase synthesis gas-to-DME process in which both catalysts for methanol synthesis and the methanol dehydration reactions deactivate rapidly.

Natural Gas Conversion VIII, Elsevier 2007, pages 403 to 408, discloses the slurry phase DME direct synthesis technology. In FIG. 2 on page 406 the deactivation of the DME synthesis catalyst over an operation time of 0 to 350 hours is disclosed.

The references above show that the catalysts employed in the synthesis gas-to-dimethyl ether (DME) process undergo rapid deactivation.

The known processes are often not satisfying with regard to the long-term stability of the catalyst system employed.

The object underlying the present invention is to provide a multi-component catalyst system which has a significantly improved long-term stability in the direct synthesis of dimethyl ether from synthesis gas.

The object is achieved according to the present invention by a catalyst system for a continuous synthesis gas-to-dimethyl ether process, comprising two spatially separated subsequent catalyst layers 1 and 2 in flow direction, catalyst layer 1 comprising synthesis gas-to-methanol catalyst particles, catalyst layer 2 comprising an admixture of synthesis gas-to-methanol catalyst particles and methanol-to-dimethyl ether catalyst particles.

The admixture of the two different catalyst particles in catalyst layer 2 is preferably a physical mixture of two different sets of individual catalyst particles and the admixture can also comprise one set of catalyst particles each consisting of synthesis-gas-to-methanol catalyst and methanol-to-dimethyl ether catalyst.

The object is furthermore achieved by the use of a catalyst system as defined above for producing dimethyl ether from synthesis gas.

The invention also relates to a process for preparing dimethyl ether from synthesis gas, comprising administering synthesis gas to the inlet to catalyst layer 1 in a catalyst system as defined above and removing dimethyl ether-containing product gas from the outlet of catalyst layer 2.

It has been found that by employing a specific sequence of two separate subsequent catalyst layers in a catalyst system, preferably a tubular reactor, the catalyst deactivation can be minimized or at least significantly reduced.

In this process two catalysts are employed, i.e. a methanol synthesis catalyst and a methanol dehydration catalyst. The methanol synthesis catalyst can also be described as the synthesis gas-to-methanol catalyst. This catalyst catalyses the chemical reaction starting from synthesis gas and leading to methanol. Thus, when employing this catalyst, methanol is the main product when starting the reaction from synthesis gas. Other products are only formed to a minor extent.

The methanol dehydration catalyst can also be described as methanol-to-dimethyl ether catalyst. This catalyst catalyses the reaction starting from methanol and leading to dimethyl ether and water. Dimethyl ether and water are the main products and other products are only formed to a minor extent.

Both catalysts preferably catalyse side reactions not leading to the described main product only to minor extents.

The term "catalyst layer" defines a close spatial relationship of individual catalyst particles. Thus, the catalyst particles and the catalyst layers can be in direct contact with each other or in a close spatial relationship in which they are not in direct contact with each other. For example, the catalyst layers can be present as packed beds or slurries. Thus, the term "catalyst layer" is not restricted to fixed or packed beds but also encompasses situations in which individual catalyst particles are separated, e.g. by fluids.

The catalyst system can be freely chosen as long as it allows for a continuous process and for spatially separating the two subsequent catalyst layers 1 and 2.

The catalyst system is employed in one or more containments, which allow for the special separation of the subsequent catalyst layers 1 and 2. Thus, the containment has at least two sections in which the catalyst layers 1 and 2 are located, and the two sections are linked in a way that the reactants can flow from catalyst layer 1 to catalyst layer 2.

Depending on the type of catalyst layers, the catalyst system may be employed in one or more tubular reactors or in two or more tank reactors. It is also possible to employ a series of at least two loop reactors in which the respective catalyst slurries are moved in a loop. Combinations of the different catalyst systems can also be employed. The construction of the catalyst system is not further limited, as long as it allows spatial separation of the two catalyst layers 1 and 2 and their subsequent arrangement so that the reactants flow from the catalyst layer 1 to catalyst layer 2.

Typically, no methanol is isolated between catalyst layers 1 and 2. This means that typically the reaction product coming from catalyst layer 1 is directly fed to catalyst layer 2 without being further purified, concentrated or submitted to any other work-up sequence.

The catalyst layers 1 and 2 can be separated, for example by some length of tubing, by inert particle beds or other means.

The synthesis gas-to-methanol catalyst particles can be chosen from all catalyst particles that catalyse this reaction. Preferably, the catalyst particles comprise copper oxide, aluminium oxide, zinc oxide, zirconium oxide, amorphous aluminium oxide, ternary oxide or mixtures thereof, or comprise PdZn or comprise $Cr_2O_3/ZnO$. These catalyst systems are described, for example, in WO 2013/160133, WO 2013/120945 and WO 2013/120938, respectively.

The catalyst layer 2 preferably comprises a mixture of
(A) 60-80 weight-% of a methanol-active component, selected from the group consisting of copper oxide, aluminium oxide, zinc oxide, zirconium oxide, amorphous aluminium oxide, ternary oxide or mixtures thereof,
(B) 20-40 weight-% of an acid component, selected from the group consisting of aluminium hydroxide, aluminium oxide hydroxide and/or γ-aluminium oxide with 0.1-20 weight-% of niobium, tantalum, phosphorus or boron, based on component (B), or mixtures thereof, or acidic aluminium oxide like γ-aluminium oxide, alumosilicate, silicate, zeolite, niobium oxide, tantalum oxide, titanium oxide, zirconium oxide, silicon oxide, aluminium phosphate, niobium phosphate, or mixtures thereof,
(C) 0-10 weight-% of at least one additive, whereby the sum of the components (A), (B) and (C) is in total 100 weight-%.

The term "mixtures" can also mean "a mixture".

Suitable catalyst layer 2 particles are described in WO 2013/160133, WO 2013/120945 and WO 2013/120938, respectively.

Preferably, the synthesis gas-to-methanol catalyst particles in catalyst layers 1 and 2 are the same.

Catalyst layer 1 comprises the synthesis gas-to-methanol catalyst particles preferably as the only catalytically active particles. In other words, catalyst layer 1 preferably does not contain methanol-to-dimethyl ether catalyst particles.

Both catalyst layers 1 and 2 can comprise inert particles for diluting the catalyst particles. The term "inert particles" defines a particulate catalytically inactive material.

Typically, catalyst systems employed as slurries do not contain inert materials/catalytically inactive materials.

Specifically, according to one embodiment of the invention, the synthesis gas-to-methanol particles in catalyst layer 1 are in admixture with inert 1 particles. These inert 1 particles can be freely chosen as long as they do not interfere in the chemical reaction starting from synthesis gas and leading to methanol. The inert 1 particles are preferably selected from the group consisting of $Al_2O_3$, glass beads, SiC, steatite or mixtures thereof.

The catalyst system for a continuous synthesis gas-to-dimethyl ether process as outlined above preferably comprises two separate subsequent catalyst layers 1 and 2 in flow direction, the catalyst layers 1 and 2 having a volume ratio of from 9:1 to 1:9, catalyst layer 1 being formed of a packed bed of catalyst 1 particles or an admixture of catalyst 1 particles and inert 1 particles in a weight ratio of from 1:4 to 4:1, catalyst 1 comprising 5 to 80 weight-% CuO, besides ZnO, $Al_2O_3$ and optionally $ZrO_2$, inert 1 particles comprising $Al_2O_3$, catalyst layer 2 being formed of a packed bed of an admixture of catalyst 1 particles and catalyst 2 particles in a weight ratio of from 1:9 to 9:1, catalyst 2 particles being formed of an acidic aluminosilicate zeolite with a $SiO_2$:$Al_2O_3$ molar ratio of from 10 to 1500:1, comprising 10 to 90 weight-% of at least one binder material, based on the total weight of catalyst 2 particles, which is 100 weight-%.

In the following the catalyst system which can be located in one or more tubular reactors is described as a tubular reactor, which is a preferred embodiment.

In a first layer 1, a packed bed of a methanol synthesis catalyst in admixture with inert 1 particles is employed. In the second, subsequent downstream catalyst layer 2 a mixture of the methanol synthesis catalyst and a methanol dehydration catalyst is employed.

It was found, by employing specific ratios of the two catalyst beds and specific ratios of the two components in each catalyst bed in combination with a specific methanol synthesis catalyst and methanol dehydration catalyst, the deactivation of the catalyst can be minimized.

Furthermore it was found, by employing the tubular reactor comprising the two separate subsequent catalyst layers 1 and 2 according to the present invention, the maximum temperature to which the catalyst is exposed during the dimethyl ether synthesis process can be limited. Preferably, the temperature in catalyst layers 1 and 2 is kept within the range of from 200 to 400° C., more preferably 220 to 360° C., even more preferably 240 to 320° C.

Preferably, the maximum temperature in the catalyst layers 1 and 2 in the tubular reactor should be limited to 320° C. or lower, more preferably 290° C. or lower, specifically 280° C. or lower.

Furthermore, in catalyst layer 1 the minimum temperature should be preferably 240° C. or higher, more preferably 250° C. or higher, specifically 260° C. or higher.

In catalyst layer 2, the minimum temperature should be preferably 240° C. or higher, more preferably 260° C. or higher, specifically 270° C. or higher.

This leads to a preferred temperature range in catalyst layer 1 of from 240 to 320° C., more preferably 250 to 290° C., specifically 260 to 280° C.

In catalyst layer 2, the temperature range is preferably 240 to 320° C., more preferably 260 to 290° C., specifically 270 to 280° C.

Consequently, a temperature control in the catalyst layers 1 and 2 to maintain a catalyst bed temperature in the above ranges is advantageous for minimizing the catalyst deactivation.

The synthesis gas-to-dimethyl ether (DME) process according to the present invention is preferably carried out in a tubular reactor through which the synthesis gas flows and which contains the two separate catalyst layers. In flow direction of the synthesis gas, first catalyst layer 1 is passed and then catalyst layer 2. Both catalyst layers are preferably packed beds which are separate from one another, i.e. they are not mixed but spatially separated. The separation can be achieved by an interlayer of inert particles spatially separating the two catalyst layers. However, it is also possible that catalyst layer 2 directly follows catalyst layer 1, so that both catalyst layers are adjacent.

Synthesis gas, or briefly syngas, is a mixture of carbon monoxide, carbon dioxide and hydrogen. Syngas can be produced from many sources, including natural gas, coal, biomass or virtually any hydrocarbon feed store, by reaction with steam or oxygen. The formation of syngas is strongly endothermic and requires high temperatures. Steam reforming of natural gas or shale gas is typically performed in tubular reactors that are heated externally. The process typically employs nickel catalysts on a special support that is resistant against the harsh process conditions. Typically syngas with $H_2/CO$ ratios in the range of 3 to 4 is obtained in this manner.

Alternative routes to syngas are the partial oxidation of methane or other hydrocarbons yielding syngas with a $H_2/CO$ ratio of about 2.

Autothermal reforming is a hybrid which combines methane steam reforming and oxidation in one process. These and alternative routes to syngas are disclosed in J. van de Loosdrecht and J. W. Niemantsverdriet, "Chemical energy storage", R. Schlogl, Ed., De Gruyter, Berlin, 2013, Chapter "Synthesis gas to hydrogen, methanol, and synthetic fuels".

According to the present invention, syngas with $H_2/CO$ ratios in the range of from 1 to 10, preferably from 1 to 3 can be employed, or a stoichiometric number of 0.7 to 2.2.

The process according to the present invention starts from synthesis gas and leads to dimethyl ether as the desired product. The process as such is as discussed above.

The tubular reactor preferably employed according to the present invention is an elongated tube which has a diameter which is much smaller than the length of the tube. A typical tube can have a circular or ellipsoidal cross-section. Preferably, the cross-section is circular, having a diameter of preferably 1 to 5 cm, more preferably 2 to 3 cm.

The tubular reactor is preferably equipped with an external heating. Preferably, the tubular reactor possesses at least two independent heating sections for independent heating of catalyst layers 1 and 2.

Catalyst layers 1 and 2 are employed in the tubular reactor preferably in a volume ratio of from 9:1 to 1:9, preferably 1:1.5 to 1:3, more preferably 1:1.8 to 1:2.5, most preferably 1:2 to 3:4.

Typically, the volume of catalyst layer 2 is higher than the volume of catalyst layer 1 if catalyst layer 1 contains 50 weight-% of inert 1 particles.

Depending on the inner diameter of the tubular reactor, the percentage of inert 1 particles in catalyst layer 1 can be modified. Higher diameters of above 3 cm might require amounts of more than 50 weight-% inert 1 particles in catalyst layer 1 in order to achieve an adequate temperature control.

Catalyst layer 1 is preferably a packed bed of an admixture of catalyst 1 particles and inert 1 particles in a weight ratio of from 1:4 to 4:1, preferably 3:7 to 7:3, more preferably 2:3 to 3:2, for example around 1:1.

The admixture typically means that catalyst 1 particles and inert 1 particles are separately provided and then admixed so that they form a physical particle mixture.

Catalyst 1 is a methanol formation catalyst and preferably comprises 5 to 80 weight-% CuO besides ZnO, $Al_2O_3$ and optionally $ZrO_2$. The amount of CuO, based on catalyst 1 particles, is 5 to 80 weight-%, more preferably 30 to 70 weight-%, particularly 50 to 70 weight-%, especially 55 to 65 weight-%, for example 60 weight-%.

The remainder of catalyst 1 particles, ZnO, $Al_2O_3$ and optionally $ZrO_2$, are typically employed in a constant weight ratio. Based on the total weight of the catalyst 1 particle (all ingredients sum up to 100 weight-%), the amount of ZnO is preferably 10 to 30 weight-%, more preferably 15 to 25 weight-%, specifically 18 to 21 weight-%. The amount of $Al_2O_3$ is preferably 10 to 30 weight-%, more preferably 12 to 22 weight-%, more preferably 16 to 18 weight-%. The amount of $ZrO_2$, if present, is preferably in the range of from 0.5 to 5 weight-%, more preferably 1 to 4 weight-%, specifically 2 to 3 weight-%.

Preferably, catalyst 1 particles comprise, based on the total weight of catalyst 1 particles, which is 100 weight-%, 30 to 70 weight-% CuO, 10 to 30 weight-% ZnO, 10 to 30 weight-% $Al_2O_3$, 1 to 5 weight-% $ZrO_2$, and 0 to 7 weight % of further additives, e.g. 1 to 7 weight-% of a solid tableting lubricant. Further additives may be the additives typically employed in the production of catalyst particles. Reference can be made to WO 2013/120938, page 7, lines 33 ff. Other additives are disclosed in this reference as well.

Typical catalysts and inert particles employed in a slurry process have a more or less spherical shape or a particulate form that is not especially critical. When catalyst layers 1 and 2 are present as slurries, the average particle size $d_{50}$ is preferably from 50 to 500 μm. The particle size is measured with an optical particle sizer.

If packed beds are employed, typical catalyst 1 particles as well as inert 1 particles and catalyst 2 particles are extrudates with an average maximum diameter of from 1 to 3.5 mm and a ratio of average length to average maximum diameter of from 0.5:1 to 10:1.

The term "average maximum diameter" is typically measured by measuring the maximum diameter of a number of extrudates (typically 10 extrudates) and deriving the average of this diameter. For a circular cross-section, there is only one diameter of the extrudates. For a non-circular cross-section, e.g. an ellipsoidal cross-section, the maximum diameter is measured and the average over ten samples is taken.

The average length is measured in a similar manner and obtained from measuring ten extrudate samples.

Preferably, the extrudates of catalyst 1 particles, catalyst 2 particles and inert 1 particles have an average maximum diameter of from 0.5 to 5 mm, more preferably 1 to 3.5 mm, specifically 1.3 to 2.0 mm. Examples of useful diameters are 1.5 to 1.6 mm and 3 to 3.2 mm.

The ratio of average length to average maximum diameter is preferably 0.5:1 to 10:1, more preferably 1:1 to 3:1, specifically 1:1 to 2:1.

The catalyst 1 particles can be prepared as described below or as described in EP-A 1 238 701, WO 2013/120938 and WO 2013/120945 and the documents cited therein.

The inert 1 particles preferably comprise $Al_2O_3$. Thus, the inert 1 particles can be $Al_2O_3$ alone or a mixture of $Al_2O_3$ particles with other inert particles.

Since $Al_2O_3$ is present in catalyst 1 particles as well, the overall content of $Al_2O_3$ in catalyst layer 1 can be adjusted by adjusting the amounts of $Al_2O_3$ in catalyst 1 particles and inert 1 particles, respectively.

The catalyst layer 2, which follows catalyst layer 1, is preferably a packed bed of an admixture of catalyst 1 particles and catalyst 2 particles in a weight ratio of from 1:9 to 9:1, preferably 6.5:3.5 to 8.5:1.5, specifically 3:2 to 7:3.

The catalyst 1 particles employed in catalyst layers 1 and 2 can be the same.

The catalyst 2 particles are formed of an acidic aluminosilicate zeolite with a $SiO_2:Al_2O_3$ molar ratio of from 10 to 1500:1, preferably 50 to 1200:1, more preferably 200 to 1000:1, for example 280:1, 400:1 or 900:1.

Typical acidic zeolites can be chabazite, mordenite, γ-zeolite, β-zeolite, Usy or of the framework type MFI. Preferably, the acidic zeolite is of framework type MFI, specifically ZSM-5.

The catalyst 2 particles comprise 10 to 90 weight-%, more preferably 20 to 70 weight-%, specifically 30 to 50 weight-%, for example 40 weight-% of at least one binder material, based on the total weight of catalyst 2 particles. Optionally, additional transition metals like Cu can be present.

Preferably, the at least one binder material is selected from $Al_2O_3$, $SiO_2$, $TiO_2$ and $ZrO_2$. Most preferably, $Al_2O_3$ is employed as the binder material.

Optionally, 0 to 20 weight-%, more preferably 0.01 to 20 weight-%, most preferably 0.1 to 15 weight-%, specifically 0.3 to 5 weight-%, for example 0.5 weight-% of a transition metal can be employed, which is preferably selected from elements of the groups 8, 9, 10, 11 of the periodic table or a mixture thereof, most preferably Cu.

Most preferred are catalyst 2 particles which comprise ZSM-5 aluminosilicate, $Al_2O_3$ as binder material and copper.

The catalyst 2 particles can be produced as described below or according to processes similar to those disclosed for producing catalyst 1 particles.

The catalyst 2 particles are typically prepared by intimately mixing powders of the acidic zeolite and the binder material which is used in the form of the corresponding oxide, hydroxide, oxide or hydroxide materials, and, if needed a peptizing agent like organic or inorganic acids, e.g. $HNO_3$, formic acid or acetic acid, and an organic pore-forming material, like carboxymethyl cellulose. To the powder mixture a necessary amount of liquid is added so that a material is obtained which can be kneaded. The material is subsequently pressed through an orifice, so that extrudates are obtained.

The metal dopant, preferably copper, can be admixed with the powders before kneading, or extrudates can be impregnated with a solution of a soluble salt or complex of the metal.

Drying and calcining can be performed in a known manner.

The tubular reactor according to the present invention comprises the two separate and subsequent catalyst layers 1 and 2 in one or more tubular reactors. Further layers of catalyst materials or inert materials can be provided if considered necessary. According to the preferred embodiment, only catalyst layers 1 and 2 as defined above are present as catalysts in the tubular reactor. It is, furthermore, possible to employ an additional guard bed or additional layers of inert material.

The catalyst system, preferably the tubular reactor is employed in a process for preparing dimethyl ether from synthesis gas. In this process, synthesis gas is administered to the inlet to catalyst layer 1. Dimethyl ether-containing product gas is removed from the outlet of catalyst layer 2. Preferably, the temperature in the catalyst layers 1 and 2 is kept within the range as indicated above.

When running the process according to the present invention, the synthesis gas is preferably preheated and the catalyst layers 1 and 2 are preheated and the desired catalyst bed temperature is monitored and controlled separately for both catalyst beds. If necessary, the synthesis gas can be diluted by an inert gas in order to achieve the desired temperature profile.

The present invention is further illustrated by the examples below.

EXAMPLES

The tubular reactor (inner diameter of 1", total length of 2 meters) possesses two independent heating sections: heating section one from 0 to 0.8 meters, heating section two from 0.8 to 2 meters of the reactor length. Each section can be heated to a different temperature.

The two catalyst layers are filled in such a way that the catalyst layer one is located within the heating section one and the catalyst layer two is located within the heating section two. The catalyst layer one has a weight of 270 g, a volume of 330 ml and a height of 0.6 m. The catalyst layer two has a weight of 430 g, a volume of 450 ml and a height of 0.95 m.

Catalyst Layer 1

The first catalyst layer comprises a 50:50 weight-% mixture of synthesis-gas-to-methanol catalyst and an inert material alpha alumina oxide. The synthesis-gas-to-methanol catalyst contains 58.3 weight-% CuO, 19.4 weight-% ZnO, 17.0 weight-% $Al_2O_3$, 2.4 weight-% $ZrO_2$ and 2.9 weight-% graphite as lubricant for tableting to cylindrical shaped bodies with diameter and height of 3 mm.

The synthesis-gas-to-methanol catalyst is prepared in the following way: A solution of copper, aluminium, zinc and zirconium salts, the atomic Cu:Al:Zn:Zr ratio being 1:0.5: 0.3:0.03, is precipitated with a sodium hydroxide and carbonate solution at a pH of 9 and at from 25 to 50° C. The precipitate is filtered off the suspension and washed with deionized water until the washing water is free of nitrates. The precipitate is dried. The dried precipitate is calcined at from 250 to 800° C. to give a mixed oxide. The calcined material is mixed with 3 weight-% graphite powder. The mixture is formed to cylindrical tablets with a diameter and height of 3 mm.

Catalyst Layer 2

The second catalyst layer comprises an 70%:30% or 60%:40% weight-%-mixture of synthesis-gas-to-methanol catalyst just described and of methanol-to-dimethyl ether catalyst. The methanol-to-dimethyl ether catalyst contains 60 weight-% ZSM-5 zeolite as acidic component and 40 weight-% alumina oxide as binder for extrusion to cylindrical shaped bodies with diameter of 3.2 mm or 1.6 mm and a length of up to 3.2 mm. In addition, the cylindrical shaped bodies containing zeolite and alumina oxide can be impregnated with 0.5 weight-% copper.

The methanol-to-dimethyl ether catalyst is prepared in the following way: Powder of ZSM-5 zeolite is mixed together with aluminium oxide hydroxide, the weight ratio being 1.5:1. Formic acid, carboxy methyl cellulose and water is added in necessary amount to obtain material that can be kneaded. After kneading the material is pressed through an extruder die. The extruded material is dried and afterwards calcined at from 400 to 700° C. In addition, the calcined material can be further impregnated with copper. Therefore, a copper salt solution is contacted with the extruded material in necessary amount to obtain extrudates with 0.5 weight-% copper. The copper loaded material is dried and then calcined at from 200 to 350° C.

The described catalytic materials are used in the process for dimethyl ether synthesis from synthesis gas.

Comparative Example 1

The reactor is filled with 947 ml of a 60%:40% weight-%-mixture of synthesis-gas-to-methanol catalyst and of methanol-to-dimethyl ether catalyst. The synthesis-gas-to-methanol catalyst contains 58.3 weight-% CuO, 19.4 weight-% ZnO, 17.0 weight-% $Al_2O_3$, 2.4 weight-% $ZrO_2$ and 2.9 weight-% graphite as lubricant for tableting to cylindrical shaped bodies with diameter and height of 3 mm. The methanol-to-dimethyl ether catalyst contains 60 weight-% ZSM-5 zeolite as acidic component and 40 weight-% alumina oxide as binder for extrusion to cylindrical shaped bodies with diameter of 3.2 mm and a length of up to 3.2 mm.

The catalyst bed is activated with hydrogen using commonly known activation procedures. Then, a flow of 4550 NL/h of synthesis gas which comprises 62 vol-% $H_2$, 23 vol-% CO, 5 vol-% $CO_2$ and 10 vol-% Ar is applied to the catalyst bed at 70 bar. Before entering the reactor with the catalyst bed the synthesis gas is preheated to 255° C. The heating section one of the reactor is heated to 255° C. and the heating section two of the reactor is heated to 270° C. The catalyst converts the synthesis gas to the main product dimethyl ether.

The conversion of the synthesis gas to the products is monitored by gas chromatography by analysing the gas composition before and after the catalyst bed. The temperature inside the catalyst bed is measured with thermocouples located at different heights of the catalyst bed.

Example 2

The reactor is filled with two catalyst layers. The catalyst layer one, which is located at the reactor inlet within the heating section one, comprises 330 ml of a 50%:50% weight-%-mixture of synthesis-gas-to-methanol catalyst and of an inert material alpha alumina oxide. The synthesis-gas-to-methanol catalyst contains 58.3% weight-% CuO, 19.4 weight-% ZnO, 17.0 weight-% $Al_2O_3$, 2.4 weight-% $ZrO_2$ and 2.9 weight-% graphite as lubricant for tableting to cylindrical shaped bodies with diameter and height of 3 mm.

The catalyst layer two, which is located directly behind the catalyst layer one within the heating section two, comprises 450 ml of an 70%:30% weight-%-mixture of synthesis-gas-to-methanol catalyst just described and of methanol-to-dimethyl ether catalyst. The methanol-to-dimethyl ether catalyst contains 60 weight-% ZSM-5 zeolite as acidic component and 40 weight-% alumina oxide as binder for extrusion to cylindrical shaped bodies with diameter of 1.6 mm and a length of up to 3.2 mm.

The catalyst bed is activated with hydrogen using commonly known activation procedures. Then, a flow of 2205 NL/h of synthesis gas which comprises 62 vol-% $H_2$, 23 vol-% $CO_3$ 5 vol-% $CO_2$ and 10 vol-% Ar is applied to the catalyst bed at 50 bar. Before entering the reactor with the catalyst bed the synthesis gas is preheated to 255° C. Also the heating section one of the reactor with the catalyst layer one inside is heated to 255° C. The heating section two of the reactor with the catalyst layer two inside is heated to 257° C. The catalyst layer one partially converts the synthesis gas to methanol. The resulting gas, comprising methanol and unconverted synthesis gas, is subsequently directed to the catalyst layer two where the synthesis gas/methanol mixture is further converted to the main product dimethyl ether.

The conversion of the synthesis gas to the products is monitored by gas chromatography by analysing the gas composition before and after the catalyst bed. The temperature inside the catalyst bed is measured with thermocouples located at different heights of the catalyst bed.

It was found that the catalyst activity, demonstrated by conversion of synthesis gas, is less reduced over time if the catalyst bed in the reactor comprises a two layer composition (example 2) instead of one catalyst layer (comparative example 1).

Example 3

The reactor is filled with two catalyst layers. The catalyst layer one, which is located at the reactor inlet within the heating section one, comprises 330 ml of a 50%:50% weight-%-mixture of synthesis-gas-to-methanol catalyst and of an inert material alpha alumina oxide. The synthesis-gas-to-methanol catalyst contains 58.3% weight-% CuO, 19.4 weight-% ZnO, 17.0 weight-% $Al_2O_3$, 2.4 weight-% $ZrO_2$ and 2.9 weight-% graphite as lubricant for tableting to cylindrical shaped bodies with diameter and height of 3 mm.

The catalyst layer two, which is located directly behind the catalyst layer one within the heating section two, comprises 450 ml of an 700%:3020% weight-%-mixture of synthesis-gas-to-methanol catalyst just described and of methanol-to-dimethyl ether catalyst. The methanol-to-dimethyl ether synthesis catalyst contains 60 weight-% ZSM-5 zeolite as acidic component and 40 weight-% alumina oxide as binder for extrusion to cylindrical shaped bodies with diameter of 1.6 mm and a length of up to 3.2 mm. In addition, the cylindrical shaped bodies containing zeolite and alumina oxide are impregnated with 0.5 weight-% copper.

The catalyst bed is activated with hydrogen using commonly known activation procedures. Then, a flow of 2152 NL/h of synthesis gas which comprises 62 vol-% $H_2$, 23 vol-% $CO_3$ 5 vol-% CO2 and 10 vol-% Ar is applied to the catalyst bed at 50 bar. Before entering the reactor with the catalyst bed the synthesis gas is preheated to 256° C. Also the heating section one of the reactor with the catalyst layer one inside is heated to 256° C. The heating section two of the reactor with the catalyst layer two inside is heated to 260° C. The catalyst layer one partially converts the synthesis gas to methanol. The resulting gas, comprising methanol and unconverted synthesis gas, is subsequently directed to the catalyst layer two where the synthesis gas/methanol mixture is further converted to the main product dimethyl ether.

The conversion of the synthesis gas to the products is monitored by gas chromatography by analysing the gas composition before and after the catalyst bed. The temperature inside the catalyst bed is measured with thermocouples located at different heights of the catalyst bed.

It was found that the catalyst activity, demonstrated by conversion of synthesis gas, is even less reduced over time if the dimethyl ether synthesis catalyst is impregnated with 0.5 weight-% copper (example 3) compared to the copper-free dimethyl ether synthesis catalyst (example 2).

The catalyst deactivation in examples 1 to 3 was determined by measuring the relative catalyst activity in dependence on the time-on-stream in a range of from 25 to 400 hours. The relative catalyst activity was determined from the product gas composition. The following deactivation in %/h was obtained.

Example 1: 0.04
Example 2: 0.02
Example 3: 0.001.

The temperature in the catalyst bed in the heating section 2 was 265 to 282° C. in example 1, 270 to 278° C. in example 2 and 270 to 275° C. in example 3.

The invention claimed is:

1. A catalyst system for a continuous synthesis gas-to-dimethyl ether process, comprising two spatially separated subsequent catalyst layers 1 and 2 in flow direction, the catalyst layers 1 and 2 having a volume ratio of from 9:1 to 1:9, catalyst layer 1 being formed of a packed bed of synthesis gas-to-methanol catalyst 1 particles or an admixture of catalyst 1 particles and inert 1 particles in a weight ratio of from 1:4 to 4:1, catalyst 1 particles comprising based on the total weight of catalyst 1 particles, which is 100 weight-%, 30 to 70 weight-% CuO, 10 to 30 weight-% ZnO, 10 to 30 weight-% $Al_2O_3$, the amount of $ZrO_2$, if present, is in the range of from 0.5 to 5 weight-%, 0 to 7 weight-% of further additives, inert 1 particles comprising $Al_2O_3$, catalyst layer 2 being formed of a packed bed of an admixture of catalyst 1 particles and methanol-to-dimethyl ether catalyst 2 particles in a weight ratio of from 1:9 to 9:1, catalyst 2 particles being formed of an acidic aluminosilicate zeolite with a $SiO_2 \geq Al_2O_3$ molar ratio of from 10 to 1500:1 of framework type MFI, comprising based on the total weight of catalyst 2 particles, which is 100 weight-%, 10 to 90 weight-% of at least one binder material, selected from $Al_2O_3$, SiO2, TiO2 and ZrO2, and 0.01 to 20 weight-% of copper,
wherein the catalyst system is employed in one or more containments, which allow for the spatial separation of the subsequent catalyst layers 1 and 2, the containment having at least two sections in which the catalyst layers 1 and 2 are located, and the two sections being linked in a way that reactants can flow from catalyst layer 1 to catalyst layer 2.

2. The catalyst system according to claim 1, wherein catalyst layer 2 directly follows catalyst layer 1 or is separated from it by a layer of inert particles.

3. The catalyst system according to claim 1, wherein the catalyst 1 particles comprise, based on the total weight of catalyst 1 particles, which is 100 weight-%, 30 to 70 weight-% CuO, 10 to 30 weight-% ZnO, 10 to 30 weight-% $Al_2O_3$, 1 to 5 weight-% $ZrO_2$, 0 to 7 weight-% of further additives.

4. The catalyst system according to claim 3, wherein the further additives comprise 1-7 weight-% of a lubricant.

5. The catalyst system according to claim 1, wherein the catalyst 2 particles comprise, based on the total weight of catalyst 2 particles, which is 100 weight-%, 30 to 80 weight-% of at least one acidic aluminosilicate of framework type MFI, 20 to 70 weight-% of at least one binder material selected from Al2O3, SiO2, TiO2 and ZrO2, and 0.01 to 20 weight-% copper.

6. The catalyst system according to claim 5, wherein the catalyst 2 particles comprise ZSM-5 aluminosilicate, $Al_2O_3$ as binder material and copper.

7. The catalyst system according to claim 1, wherein catalyst layer 2 is formed of a packed bed of an admixture of catalyst 1 particles and catalyst 2 particles in a weight ratio of from 3:2 to 7:3.

8. The catalyst system according to claim 1, wherein the catalyst 1 particles, catalyst 2 particles and inert 1 particles have each an average maximum particle diameter of from 0.5 to 5 mm.

9. The catalyst system according to claim 1, wherein the catalyst system is located in one or more tubular reactors.

10. The catalyst system according claim 1, wherein the catalyst layers 1 and 2 are present as packed beds and wherein the catalyst 1 particles, catalyst 2 particles and inert 1 particles are extrudates with an average maximum diameter of from 1 to 3.5 mm and a ratio of average length to average maximum diameter of from 0.5:1 to 10:1.

11. A process for producing dimethyl ether which comprises converting synthesis gas by contacting the synthesis gas with the catalyst system as claimed in claim 1.

12. A process for preparing dimethyl ether from synthesis gas, comprising administering synthesis gas to catalyst layer 1 in a catalyst system as defined in claim 1, and removing dimethyl ether-containing product gas from catalyst layer 2.

13. The process of claim 12, wherein temperature in catalyst layers 1 and 2 are maintained within a temperature range of from 200 to 400° C.

14. The process of claim 13, wherein catalyst layer 1 is maintained at a temperature within the range of from 260 to 280° C. and catalyst layer 2 is maintained at a temperature within the range of from 270 to 280° C.

* * * * *